(12) United States Patent
Neuschäfer

(10) Patent No.: US 8,591,228 B2
(45) Date of Patent: Nov. 26, 2013

(54) INJECTION CORRECTION IMPRESSION TRAY

(76) Inventor: Gerd Neuschäfer, Bad Hersfeld (DE)

( * ) Notice: Subject to any disclaimer, the term of this patent is extended or adjusted under 35 U.S.C. 154(b) by 380 days.

(21) Appl. No.: 12/557,672

(22) Filed: Sep. 11, 2009

(65) Prior Publication Data
US 2010/0021858 A1    Jan. 28, 2010

Related U.S. Application Data

(63) Continuation-in-part of application No. PCT/EP2008/001922, filed on Mar. 11, 2008.

(30) Foreign Application Priority Data

Mar. 13, 2007    (DE) .......................... 10 2007 012 540

(51) Int. Cl.
*A61C 11/00* (2006.01)

(52) U.S. Cl.
USPC .................................. 433/37; 433/45; 249/54

(58) Field of Classification Search
USPC ............. 433/34–48, 213–214, 229; D24/181; 128/861–862; 249/54, 107, 109–110; 425/566, 571, 573
See application file for complete search history.

(56) References Cited

U.S. PATENT DOCUMENTS

| 2,113,223 A * | 4/1938 | Salabes ........................... 205/73 |
| 4,459,107 A * | 7/1984 | Weissman ....................... 433/36 |
| 6,149,426 A * | 11/2000 | Singer et al. ................... 433/37 |
| 6,394,802 B1 | 5/2002 | Hahn |
| 6,398,550 B1 * | 6/2002 | Caritg ............................. 433/37 |
| 6,817,861 B1 * | 11/2004 | Roetzer .......................... 433/37 |
| 6,964,568 B1 * | 11/2005 | Segal ............................. 433/45 |
| 2007/0054237 A1 | 3/2007 | Neuschäfer |

FOREIGN PATENT DOCUMENTS

| DE | 43 04 421 C1 | 8/1994 |
| DE | 195 26 017 C1 | 8/1996 |
| DE | 196 08 546 A1 | 9/1997 |

(Continued)

OTHER PUBLICATIONS

International Search Report from co-pending related PCT application No. PCT/EP2008-001922, dated Oct. 11, 2008.

*Primary Examiner* — Cris L Rodriguez
*Assistant Examiner* — Edward Moran
(74) *Attorney, Agent, or Firm* — Thomas|Horstemeyer, LLP

(57) ABSTRACT

An injection correction impression tray (18) serves for producing dental impressions for the subsequent manufacture of crowns, bridges and other dental prostheses. The tray (18) includes a base body (23) containing impression material and a profile bottom plate (27). The plate (27) includes a first channel (41) and a second channel (43) being arranged in the bottom side of the plate (27). The plate (27) is connected to the base body (23) in a way to close the bottom opening (6) of the tray (18) and such that the bottom side and the channels (41, 43) face the interior of the base body (23). The first channel (41) forms a rib of a first impression material being introduced into the interior of the base body (23) and flowing through the bottom opening (6) into the first channel (41). The first channel (41) is designed and arranged such that a channel for introducing correction impression material is formed by the first channel (41) and a remainder of the first impression material after the rib of the first impression material has been partly removed.

6 Claims, 7 Drawing Sheets

(56) References Cited

FOREIGN PATENT DOCUMENTS

| | | | |
|---|---|---|---|
| DE | 200 21 854 U1 | 5/2001 | |
| DE | 299 20 226 U1 | 5/2001 | |
| DE | 201 05 176 U1 | 7/2001 | |
| DE | 201 04 943 U1 | 10/2001 | |
| DE | 100 20 894 A1 | 11/2001 | |
| DE | 200 10 403 U1 | 11/2001 | |
| DE | 101 53 245 A1 | 5/2003 | |
| DE | 203 08 413 U1 | 9/2003 | |
| DE | 10 2005 042 013 A1 | 3/2007 | |
| DE | 102005042013 A1 | * | 3/2007 |
| EP | 1 759 659 A1 | 3/2007 | |

* cited by examiner

INJECTION CORRECTION IMPRESSION TRAY

CROSS REFERENCE TO RELATED APPLICATIONS

This application is a continuation-in-part of International Application PCT/EP2008/001922 with an International Filing Date of Mar. 11, 2008 and claiming priority to co-pending German Patent Application No. 10 2007 012 540.4 entitled "Injektionskorrektur-abformlöffel zur Direkt-, Abzweig- und Reihenbefüllung mit Korrekturabformmasse", filed on Mar. 13, 2007.

FIELD OF THE INVENTION

The present invention generally relates to an apparatus for producing dental impressions including an injection correction impression tray.

The impressions of the jaw including teeth are taken for the subsequent manufacture of crowns, bridges and other dental prostheses. The general technique described herein is the so called "injection correction impression" technique. This technique includes at least the steps of producing a first impression with a first impression material and of producing a second impression, the so called "correction impression". In the first step, an impression of the teeth is produced with a first high-viscosity impression material. In another step, a more exact correction impression is produced. During this step, a low-viscosity correction impression material is used as a correction material to produce an impression of portions of the teeth which were not accessible during the first step. For this purpose, the correction impression material is injected into the interior of the tray and into the first impressions located therein.

BACKGROUND OF THE INVENTION

An apparatus for producing injection correction impressions of a jaw including teeth is generally known in the art. The apparatus includes a tray which has a bottom side and side surfaces forming a chamber for containing impression material. The tray including a high-viscosity impression material is introduced into the mouth of the patient, and the patient closes the mouth such that the teeth enter the impression material. In this way, a first impression is produced with the first high-viscosity impression material. After hardening of the impression material, the tray is removed from the mouth of the patient. Next, the hardened impression material is partly removed to produce an injection channel for a correction impression material to be used in a following step. The tray is then reintroduced into the mouth of the patient in the same position, and a low-viscosity correction impression material is injected into the injection channel and into portions within the tray which were not accessible during the first step using the high-viscosity impression material. The known apparatus and method conducted therewith may lead to defective impressions due to saliva, blood, air, turbulences and other anatomic influences such as the tongue, the cheek bands and so forth. Such defects may result in the necessity of having to repeat the production of the impression or to insufficient prosthetic results. Thus, the known method is time consuming, stressful, expensive and takes a lot of work.

An apparatus for producing injection correction impressions of a jaw containing teeth is known from U.S. Pat. No. 6,398,550 B1 corresponding to German Gebrauchsmuster DE 200 10 403 U1 and DE 299 20 226 U1. A similar apparatus is known from German Gebrauchsmuster DE 203 08 413 U1. The know apparatus includes an injection correction impression tray having an interior for containing an impression material. The tray includes a closed bottom side into which an impression material is introduced. Furthermore, a casting channel mould can be inserted into the tray. The casting channel mould is removed after having produced the first impression, and the injection channel resulting therefrom is used for the following production of the correction impression.

Another apparatus for producing an injection correction impression of a jaw including teeth is known from German Gebrauchsmuster DE 201 05 176 U1. The apparatus includes an injection correction impression tray having an interior for containing an impression material. The tray has a bottom opening. The apparatus further includes a bottom plate being designed and arranged to be connected to the tray to close the bottom opening. The bottom plate has a plain bottom side which faces the interior of the tray. After having produced the first impression, the bottom plate is removed from the tray to be capable of manually removing parts of the impression material to produce an injection channel for a correction impression mass to be later introduced through the injection channel.

Other apparatuses for producing impressions of a jaw including teeth are known from German Gebrauchsmuster DE 200 21 854 U1, U.S. Pat. No. 6,394,802 B1 and German Patent Application No. DE 196 08 546 A1.

Other apparatuses in which the injection channels are located at the sidewalls in the interior of the tray are known from German Patent Application Nos. DE 100 20 894 A1 and DE 101 53 245 A1. Injection channels and drainage channels, respectively, are attained by selectively removing parts of the wall of the tray. It is not possible to individually choose variable injection channels and drainage channels.

Another method and apparatus is known from German Patent No. DE 195 26 017 C1. The correction impression material is introduced into the tray by injection nozzles which can be later closed, and the surplus of correction impression material exits the tray through outlet nozzles which can also be closed. The nozzles are located at fixed positions in the wall of the tray.

Another apparatus is known from German Gebrauchsmuster DE 201 04 943 U1. An injection channel for the correction impression material is produced by a placeholder hose which can be later removed from the first impression material. The channel is located in the first impression material inside of the tray. Thus, it is difficult to access the channel and to realize controlled application of the correction impression material.

Another apparatus is known from German Patent Application No. DE 10 2005 042 013 A1 and EP 1 759 659 A1 corresponding to US Patent Application No. US 2007/0054237 A1. The apparatus includes an injection correction impression tray and a bottom plate, the bottom plate including a positive protrusion (i.e. a rib) being arranged at its bottom side facing the interior of the tray. In this way, an injection channel for a correction impression material is formed in a position in which the bottom plate is connected to the injection correction impression tray in a way that the protrusion protrudes into the interior of the injection correction impression tray. The bottom plate is designed as a reversing bottom plate having another side being arranged opposed to the bottom side and being designed to be substantially plain.

Another apparatus is known from German Patent No. DE 43 04 421 C1. The apparatus includes an injection channel being located in the inside of the closed tray which cannot be opened. It is not possible to attain variable flow paths of an impression material.

SUMMARY OF THE INVENTION

The present invention generally relates to an apparatus for producing dental impressions for the subsequent manufacture of crowns, bridges and other dental prostheses. The apparatus serves to produce injection correction impressions of teeth being contained in a jaw.

The apparatus includes an injection correction impression tray having an interior for containing impression material. The tray includes a bottom opening. The apparatus further includes a bottom plate having a bottom side including a channel. In the connected position of the bottom plate and the injection correction impression tray, the opening of the channel faces the bottom opening of the injection correction impression tray.

With the novel apparatus, it is possible to effectively produce dental correction impressions with an apparatus which may be easily handled. The novel injection correction impression tray may be handled in a similar way as known trays which simplifies usage of the novel apparatus for the user.

The novel apparatus does not require complicated equipment, but it instead can be easily manufactured and handled. The novel apparatus is operated in a way that the channel located in the bottom plate serves to form protrusions or ribs in the first impression material. These protrusions or ribs may then be easily removed at freely choosable locations to produce channels through which correction impression material may later flow.

The injection correction impression tray may include one or more of the following features:
 1: a bottom opening
 2: a stiffening frame
 3: fixing and supporting devices
 4: valve edge forming devices
 5: sinking limiting devices
 6: sinking limiting device bearings
 7: a handle
 8: a separating means Ad 1: The bottom opening is located in the bottom of the tray and of the base body of the tray, respectively. It is arranged at a distance with respect to the bottom rim to ensure sufficient stability of the tray.

Ad 2: The stiffening frame increases the stiffness of the tray. It is dimensioned and formed and connected to the tray in an appropriate way. Stiffness may also be increased by folds and other shapes of the base body.

Ad 3: The fixing and supporting devices are located at a suitable position at the base body of the tray and at the handle, respectively. They serve to connect the base body and the bottom plate in a way that they can be fixedly connected and then disconnected in a non-destructive way.

Ad 4: The valve rim forming devices are located at the rims of the wall of the base body of the tray. They are designed to form a valve rim with the first impression material.

Ad 5: The sinking limiting devices during the first molding step limit the movement of the teeth into the first impression material, and they thus guarantee sufficient thickness of the first impression material located between the teeth and the bottom plate. The sinking limiting devices are either fixedly connected and/or in a way to be connectable to and removable from the tray. The fixed sinking limiting devices are fixedly connected to the wall of the base body of the tray and/or the stiffening frame or they are part of the wall of the base body.

The removable sinking limiting devices preferably are designed as pins and the like being supported in bearings being located in the wall of the base body of the tray. They are removed or dislocated in case they block the flow path of the correction impression material in the first impression material.

Ad 6: The bearings for the sinking limiting devices preferably are designed as openings in the wall of the base body of the tray and of the stiffening frame, respectively. Their dimensions are coordinated with the cross-section of the sinking limiting devices. In the mounted position of the apparatus, the bottom plate stabilizes the supported mobile sinking limiting devices against unintentional movement.

Ad 7: The handle is connected to the mesial outer wall of the base body of the tray. Its design is coordinated with anatomic and ergonomic requirements and to fit to the bottom plate.

Ad 8: The separating means serve to easily separate the bottom plate from the tray.

The bottom plate may include one or more of the following features:
 1: a handle
 2: fixing and supporting devices
 3: sealing protrusions or sealing channels
 4: retention devices
 5: sidewalls
 6: channels
  one or more channels, depending on their function being called in the following
   injection channel, or
   drainage channel
  inlets and outlets depending on their association with the above mentioned channels being designated in the following as
   injection channel inlet and injection channel outlet or drainage channel outlet or drainage channel inlet
 7: inlet adapter
 8: outlet adapter
 9: a separating means
 10: closing plug Ad 1: The handle of the profile bottom plate is arranged in the mesial portion, and it has a shape such that its fits to the handle of the base body of the tray in the mounted position. It includes separating means for simplifying detachment of the bottom plate and the base body of the tray.

Ad 2: The bottom plate includes fixing and supporting devices being located at a suitable position, the devices connecting the bottom plate and the base body of the tray in a detachable way.

Ad 3: Sealing protrusions and sealing channels, respectively, are located at the side of the bottom plate at which the channel is located. The sealing protrusions and channels, respectively, form channels and protrusions, respectively, in the first impression material. These protrusions and channels, respectively, improve sealing of the injection channel and of the drainage channel, respectively, preventing the correction impression material from draining away during the production of the correction impression.

Ad 4: Retention devices may be located at the top side of the bottom plate, i.e. the side opposite to the side including the channels. They are filled with high-viscosity impression mass (for example the first impression mass) in which the teeth of the counter jaw engage during production of the first impression. The teeth of the counter jaw engage these impressions during the later process of producing a correction impression, and they ensure that the tray is fixedly located at the desired place due to the biting pressure applied by the patient.

The bottom plate may include sidewalls or removable elements similar to sidewalls serving to contain impression mass.

Ad 6: The surface of the bottom plate facing the interior of the tray in the mounted position of the apparatus includes at least one injection channel extending over both legs of the plate. It includes at least one injection channel inlet which preferably is arranged in the mesial portion of the profile bottom plate. At least one injection channel outlet is preferably arranged at each distal end of the injection channel. It is also possible to arrange a plurality of injection channels in the bottom plate, for example one injection channel in each leg of the bottom plate and/or an additional injection channel in the region of the front teeth. These channels include at least one injection channel inlet and at least one injection channel outlet being arranged at suitable positions.

Ad 7: In addition to the at least one injection channel, the profile bottom plate includes at least one drainage channel. The drainage channel preferably is arranged approximately parallel to the injection channel, and it includes at least one drainage channel outlet preferably being arranged in the mesial portion of the profile bottom plate.

Ad 8: To simplify application of the correction impression material and for realizing an optimal connection of the impression material applicator, the injection channel inlet has a suitable shape and it includes an inlet adapter. The inlet adapter may be part of the profile bottom plate, or it may be designed as a separate device being connectable to and detachable from the injection channel inlet.

Ad 9: The drainage channel outlet has a suitable shape and it includes an outlet adapter to allow for connection of a source of negative pressure (for example a suction device). The outlet adapter may be part of the profile bottom plate, or it may be designed as a separate apparatus being connectable to and detachable from the drainage channel outlet. The connection of the suction device to the drainage channel outlet of the injection correction impression tray being filled with correction impression material and being located in the mouth of the patient serves to realize the following effects:

a) Drying the flow paths and the preparation chamber. The sucked in air streams into the injection opening and through the flow paths serving for containing the correction impression material and through the preparation chambers to the outlet opening. This results in humidity being absorbed and removed.

b) Producing a negative pressure in the preparation chamber and in the flow path system. Closing the injection channel inlet with an applicator results in a negative pressure prevailing in the flow path system and in the preparation chamber, the negative pressure increasing the flow properties and the impression forming properties of the correction impression material.

Ad 10: The separating means serve to simplify detachment of the profile bottom plate from the base body of the tray.

Ad 11: The inlet openings and outlet openings and the inlet adapter and the outlet adapter, respectively, can be closed by closing plugs which can be later removed. The closing plugs may be designed as single plugs corresponding to each of the associated openings or as a combined plug unit serving to close a plurality of the openings or even all openings. The plugs can only enter the profile bottom plate until they reach the associated injection channel and the drainage channel, respectively. They serve to prevent the first impression material from entering the injection openings and the drainage openings, respectively. Otherwise, the material would harden in these openings, and its retention would impede disassembly of the bottom plate from the tray.

The profile bottom plate and the tray are designed and shaped such that they can be interconnected in a position in which the bottom opening of the tray is closed by the bottom plate. It is to be understood that the bottom plate can later be removed from the tray. The at least one channel located in the bottom plate faces the interior of the tray in this position.

In case the thickness of the profile bottom plate is not sufficient, the walls of the channels could also extend into the other side of the bottom plate, meaning the other side does not necessarily have to be plain.

The cross-section of the channel preferably is semi-circular, U-shaped or V-shaped, and it is dimensioned to correspond to the viscosity of the correction impression material. The cross-section of the channels may also vary to control the injection pressure and the flow properties of the correction impression material.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
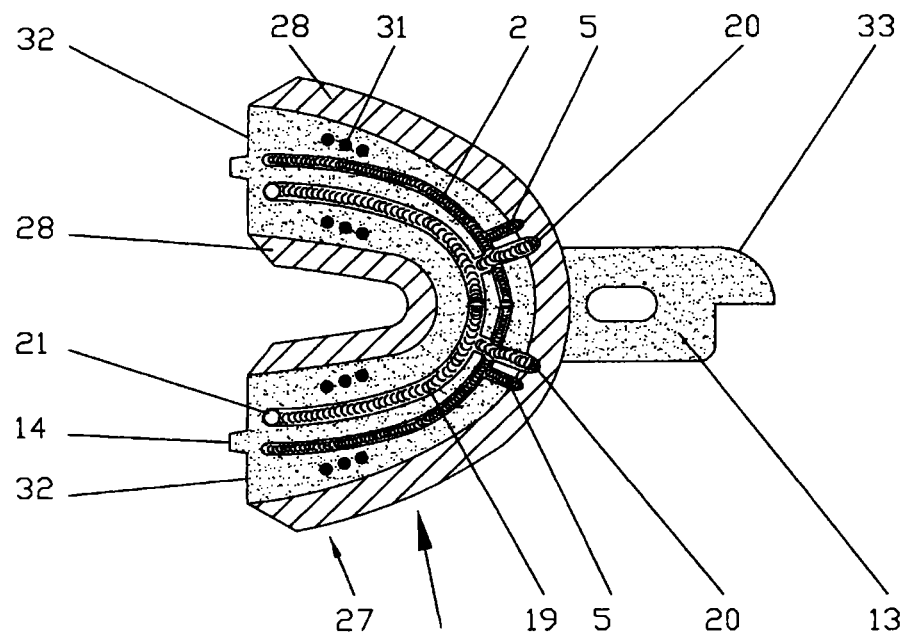
FIG. 1 is a top view of the bottom surface of the profile bottom plate.

Referring now in greater detail to the drawings, FIG. 1 illustrates the bottom surface of the profile bottom plate 27 including sidewalls 28, a continuous injection channel 19 and two injection channel inlets 20. Each leg of the profile bottom plate 27 includes a distal injection channel outlet 21 and a continuous drainage channel 2 including two mesial drainage channel outlets 5. The channels are designed as impressions in the bottom side of the profile bottom plate 27.

Figure 2:
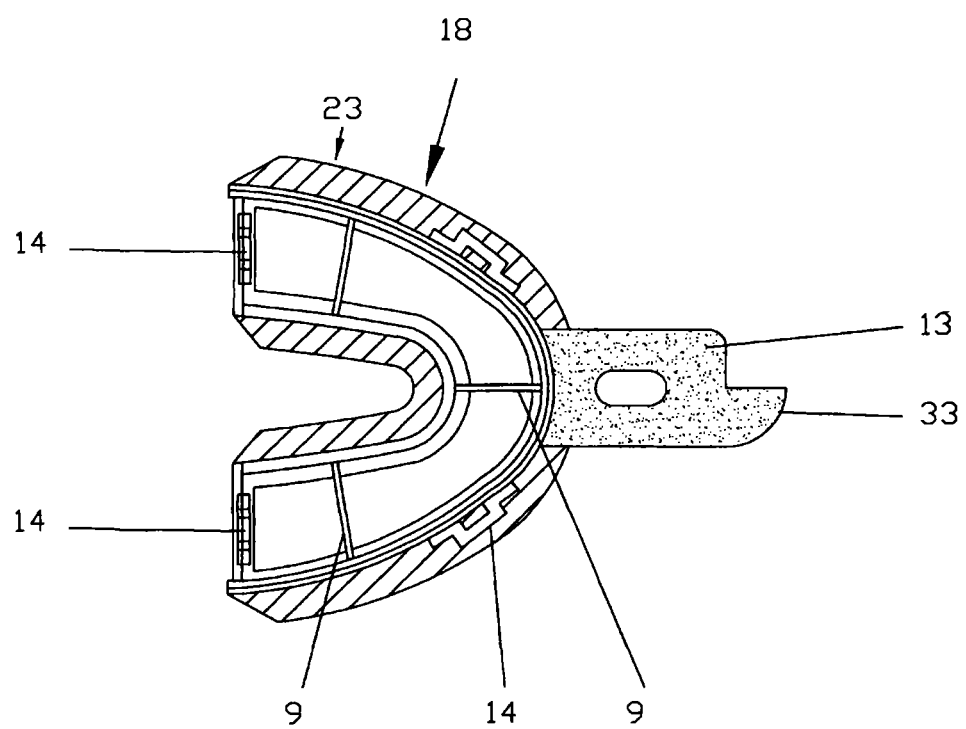
FIG. 2 is a top view of the bottom side of the base body of the tray.

FIG. 2 illustrates the bottom side of the base body 23 of the tray 18.

Figure 3:
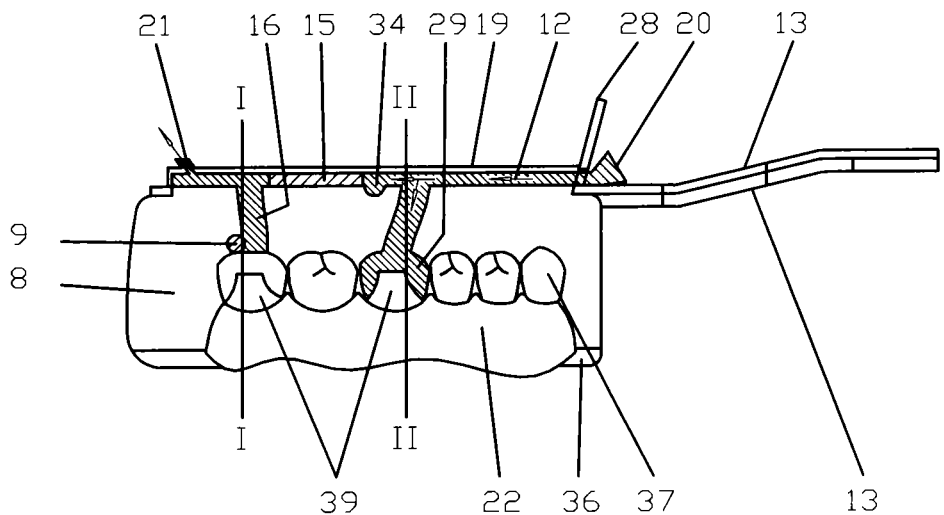
FIG. 3 is a schematic sectional view of the novel apparatus being placed on a lower jaw.

FIG. 3 schematically illustrates a longitudinal sectional view through the legs 32 of the tray 18 during production of a correction impression. The injection correction impression tray 18 is located on the lower jaw of a patient. The tooth stumps 39 are contacted by correction impression material. The flow path is illustrated by arrows. In an embodiment, the first channel has a first diameter and the at least two second channels have a second diameter, the first diameter of the first channel being greater than the second diameter of the second channels.

Figure 4:
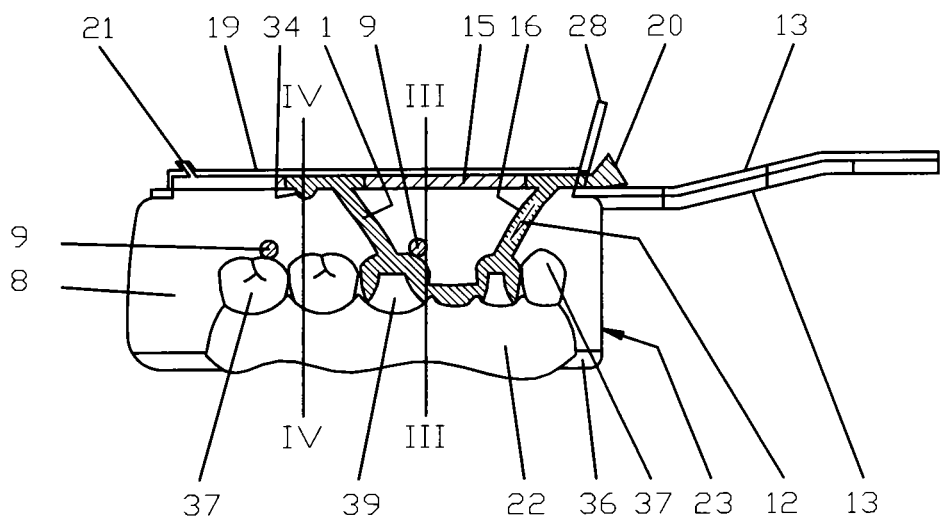
FIG. 4 illustrates another schematic sectional view of the novel apparatus being placed on a lower jaw.

FIG. 4 schematically illustrates a longitudinal sectional view through one leg 32 of the tray 18 while the tooth stumps 39 are contacted by correction impression material. The injection correction impression tray 18 is located on the lower jaw of a patient. The flow paths are illustrated by arrows.

Figure 5:
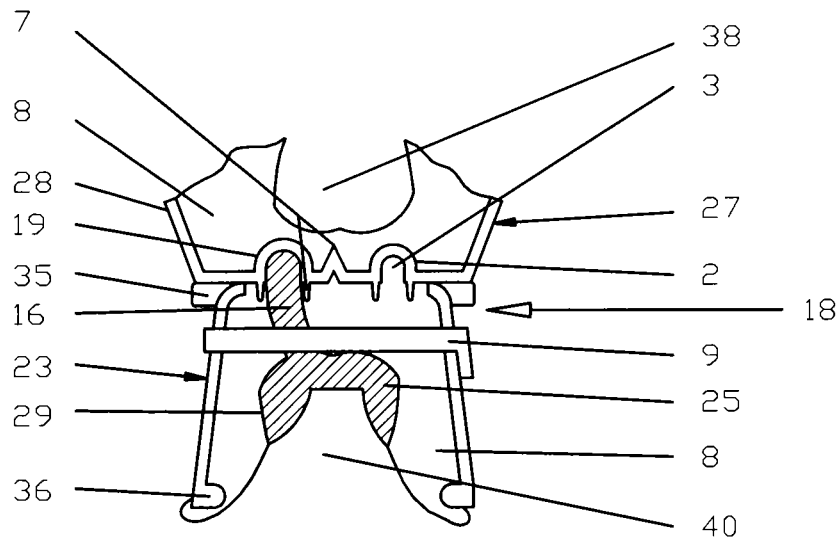
FIG. 5 is a schematic sectional view along I in FIG. 3.

FIG. 5 illustrates a sectional view along line I in FIG. 3 through the leg 32 of the injection correction impression tray 18. The profile bottom plate 27 includes sidewalls 28. The injection correction impression tray 18 is located outside of the mouth of the patient.

Figure 6:
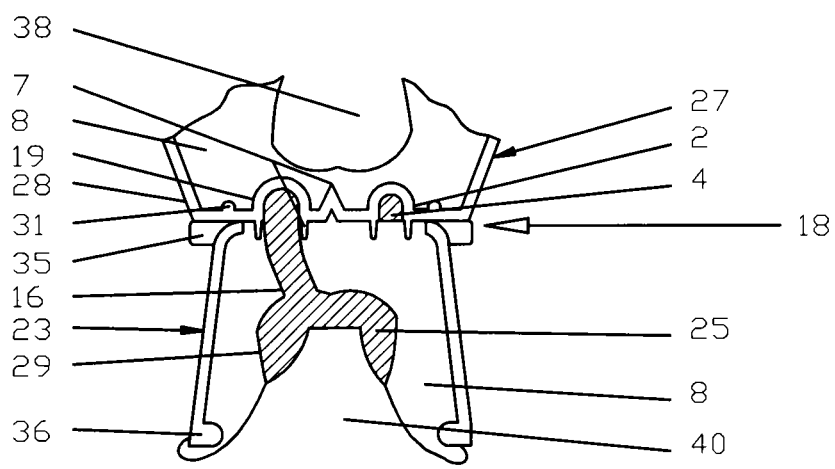
FIG. 6 is a schematic sectional view along II in FIG. 3.

FIG. 6 illustrates a sectional view along line II through the leg 32 of the injection correction impression tray 18. The profile bottom plate 27 includes sidewalls 28. The injection correction impression tray 18 is located outside of the mouth of the patient.

Figure 7:
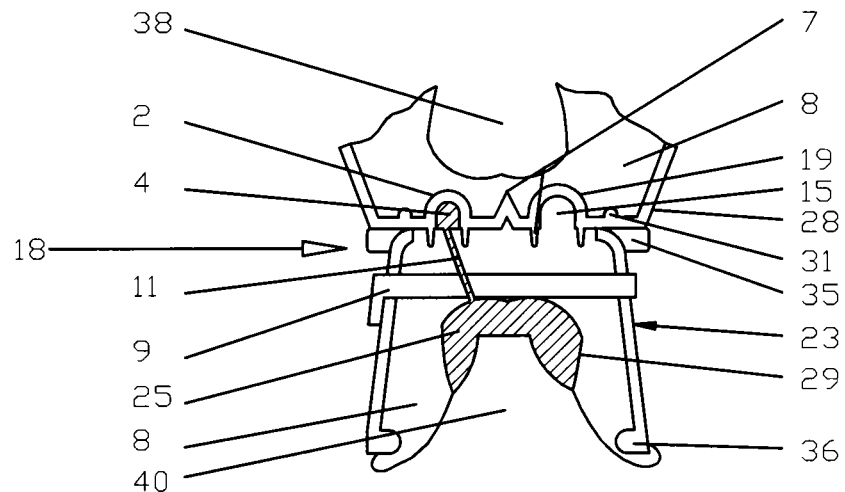
FIG. 7 is a schematic sectional view of III in FIG. 4.

FIG. 7 illustrates a sectional view along line III in FIG. 4 through the leg 32 of the injection correction impression tray 18 including a deaerating channel 11. The injection correction impression tray 18 is located outside of the mouth of the patient.

Figure 8:
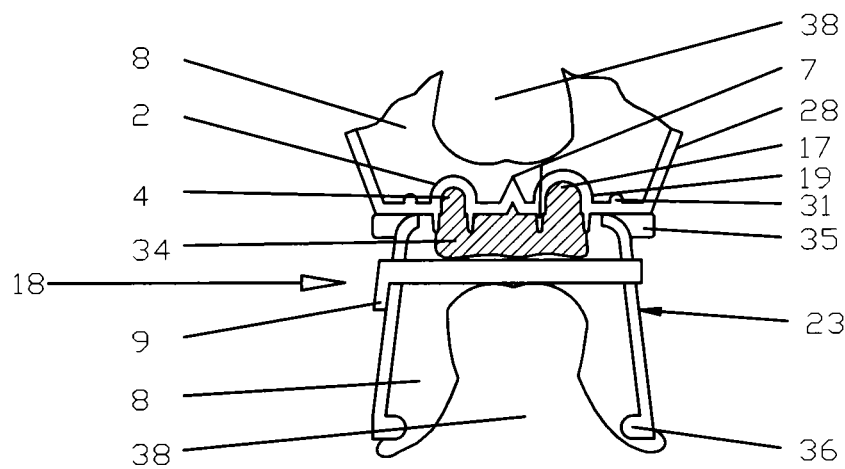
FIG. 8 is a schematic sectional view along IV in FIG. 4.

FIG. 8 illustrates a sectional view along line IV in FIG. 4 in the position of tooth 37. A connecting channel 34 is located between the injection channel 17 and the drainage channel 4. The injection correction impression tray 18 is located outside of the mouth of the patient.

Figure 9:
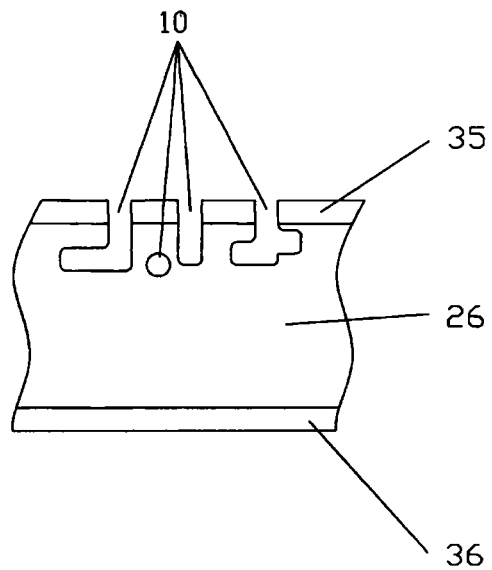
FIG. 9 is a schematic view of a part of the sidewalls of the base body of the tray.

FIG. 9 schematically illustrates a part of the walls 26 of the tray 18 including different sinking limiting device bearings 10.

In the following, the production of a dental impression by using a correction impression material 25 is explained in greater detail. The apparatus includes an injection correction impression tray 18 including a base body 23 and a profile bottom plate 27. The profile bottom plate 27 may include sidewalls 28, a continuous injection channel 19 and two injection channel inlets 20. Each leg 32 includes a distal injection channel outlet 21 and a continuous drainage channel 2 including two drainage channel outlets 5.

Before the teeth are prepared for a connection to a crown, a bridge or a different dental prosthesis, an impression of the lower jaw, for example, with high-viscosity first impression material 8 is produced. The interior 24 of the base body 23 is filled with first impression material 8. The material 8 is also introduced between the sidewalls 28 of the profile bottom plate 27 facing away from the interior 24 of the tray 18. The first impression material 8 is intended to surround the sinking limiting devices 9 in the interior 24 of the base body 23 and to fully fill the space between the sinking limiting devices 9 and the profile bottom plate 27. The injection channel 19 and the drainage channel 2 located in the surface of the profile bottom plate 27 facing the interior 24 of the injection correction impression tray 18 are also filled with first impression material 8. The injection correction impression tray 18 being filled with first impression material 8 in this way is now introduced into the mouth of the patient and located on the lower jaw and moved towards the lower jaw in a downward direction resulting in the teeth and the jaw structure entering the first impression material 8.

The sinking depth is limited by sinking limiting devices 9 preventing the teeth from contacting the bottom surface of the profile bottom plate 27. It is intended that first impression material 8 flows over the outer rims of the walls 26 of the base body 23 in a way to form a valve rim when the teeth are lowered into the injection correction impression tray 18. The valve rim seals the interior of the tray 18 against the oral cavity such that saliva does not enter the interior of the apparatus. After having placed the tray 18 on the bottom jaw, the jaws are closed until the teeth of the counter jaw enter the first impression material 8 being located on the opposite side of the profile bottom plate 27. The jaws remain in this position until the first impression material has hardened. When this has been achieved, the tray 18 is removed from the mouth and the teeth are prepared in the desired way.

In the next step, the profile bottom plate 27 is removed from the base body 23 of the injection correction impression tray 18 to get prepared for the correction impression being produced. Now, the hardened first impression material 8 is freely accessible over the extension of the entire bottom opening 6. The surface of the material 8 at this place corresponds to the shape of the channel of the profile bottom plate 27. In other words, the injection channel 19 and the drainage channel 2 have been filled with first impression material 8 such that protrusions or ribs have been produced. The sealing protrusions/sealing channels 7 now have formed impressions and protrusions, respectively.

In the next step, flow paths for the correction impression material 25 leading to the preparation chambers 29 are produced in the first impression material 8. For directly filling a first tooth, an injection cut 16 is formed in the first impression material 8, for example by a suitable hollow knife, to realize a connection to the impression of the tooth. The injection rib 15 is removed in a region between the injection cut and the injection cut 16 and the injection channel outlet 21. An injection cut 16 is also produced in the first impression material 8 to fill the other tooth as illustrated. This channel is intended to be connected to the injection rib 15. This rib 15 is removed from the connecting point to the next injection channel inlet 20. Furthermore, a connecting channel 34 between the injection channel 17 and the drainage rib 3 is formed in the first impression material 8 in a location distal to the injection cut 16. The drainage rib 3 is removed from that place to the next drainage channel outlet 5. In this way, flow paths 12 of the correction impression material 25 are produced in the fourth quadrant. These flow paths 12 are schematically illustrated in FIGS. 3, 5 and 6. For filling the preparation chamber 29 about the tooth stumps in the sense of series filling, an injection cut 16 is produced in the injection rib 15, the cut 16 realizing a connection to the tooth. The injection rib 15 is removed between the injection cut 16 and the next injection inlet 20. A connecting channel 34 is produced between the teeth. A drainage cut 1 connecting the tooth impression and the injection rib 15 being located there above is produced, and the injection rib is then removed in this portion. A connecting channel 34 to the drainage rib 3 is then produced, and the rib 3 is removed between that place and the next drainage outlet. In this way, one attains a flow path 12 of the correction impression material 25 for this quadrant. This is schematically illustrated in FIGS. 4, 7 and 8.

Deaerating channels 11 being connected to the drainage channel 4 are produced at a suitable location, preferably at the lowermost location of the tooth impressions of the prepared teeth. The deaerating channel 11 serves to deaerate the preparation chamber 29 when being filled with correction impression material 25.

After having produced the flow paths 12, the base body 23 is once again placed on the lower jaw 25, the teeth 37 and the jaw structures entering the impressions that have been produced during the first dental impression production. The places where impressions are to be taken are now dried with air via the injection cuts that have been produced in the first impression material 8. In the following, correction impression material 25 is supplied to the tooth stump by an applicator via the injection cut 16 such that it enters the preparation chamber 29. The material 25 is pressed into the tray 18 with surplus. Afterwards, the profile bottom plate 27 is connected to the base body 23, the surplus of the correction impression material 25 exiting the tray 18 through the injection channel outlet 21. When the profile bottom plate 27 is connected to the base body 23, the remaining parts of the drainage rib 3 and the injection rib 15 are supported in the injection channel 19 and the drainage channel 2, respectively, of the profile bottom plate 27. At the locations where parts of the ribs 19, 2 have been removed, the walls of the channels and the first impression material 8 in the portion where the ribs have been removed now form the injection channel 17 and the drainage channel 4. The supported sealing protrusions/sealing channels 7 prevent the correction impression material 25 from exiting the channels.

The jaws are now closed resulting in the teeth of the counter jaw entering the tooth impressions 38 in the first impression material 8 on the opposite side of the profile bottom plate 27. The position of the tray 18 on the lower jaw 22 is fixed by a controlled biting pressure. The correction impression material 25 is now pressed into the respective injection channel 17 via the associated injection inlet 20 at controlled pressure.

The correction impression material 25 may flow through the flow path 12 being formed in the first impression material 8 to reach the tooth stump. Due to gravity, it flows downwardly into the preparation chamber 29. The surplus correction impression material 25 being further pressed into the tray 18 flows through the connecting channel 34 being formed in the first impression material 8 to the drainage channel 4 and from there to the drainage outlet 5. At this place, it exits the injection correction impression tray 18.

Another possibility is that the correction impression material 25 flows along the flow path 12 to the tooth stump and via the connecting channel 34 to another tooth stump. Due to the drainage cut 1, it is guided via the distal injection channel to the connecting channel 34 to the drainage channel 4. It then exits the correction impression tray 18 through the outlet channel 5. Due to the deaerating channels 11 being formed in the first impression material 8, persisting air and remainders of liquid are dislocated from the preparation chamber into the drainage channel due to the increasing correction impression material 25. Thus, the impression is produced free from bubbles.

To optimize the flowing properties and the impression producing properties, it is possible to produce a negative pressure in the respective preparation chamber 29 before or when it is filled with correction impression material 25. The negative pressure is produced by connecting a source of negative pressure (a saliva sucking device, for example) to the respective drainage outlet 5 while simultaneously closing the injection channel inlets 20 with the applicator in an airtight manner.

When the correction impression material 25 has hardened, the injection correction impression tray 18 is removed from the mouth of the patient, and it is used for further processing in a known way for producing crowns, bridges and other dental prostheses.

With respect to the design of another embodiment of the injection correction impression tray 18 including the base body 23 and the profile bottom plate 27 which can be connected to and disconnected from the base body 23 and with respect to the functionality of the injection correction impression tray 18, it is now referred to FIGS. 10-13.

Figure 10:
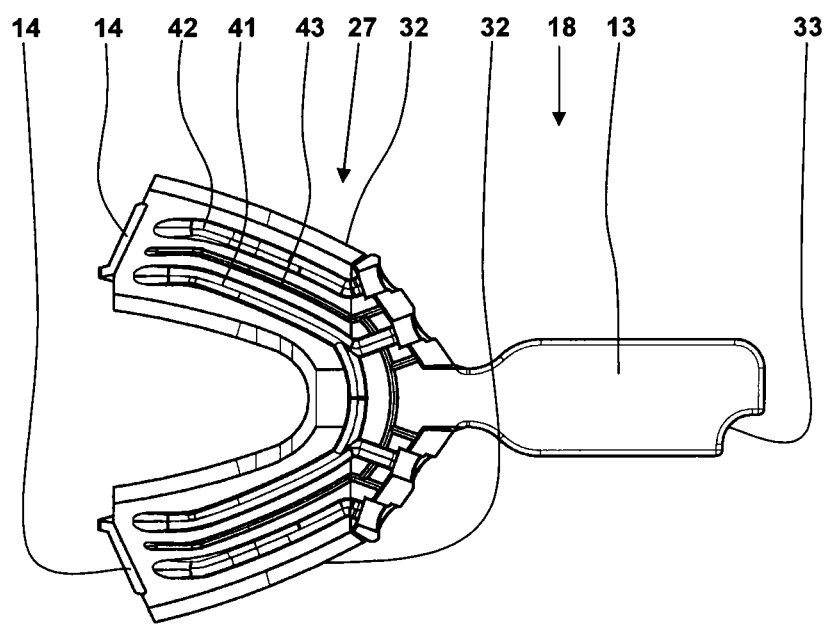
FIG. 10 is a perspective top view of another exemplary embodiment of the profile bottom plate of the novel injection correction impression tray.

FIG. 10 illustrates another exemplary embodiment of the novel injection correction impression tray 18 including the profile bottom plate 27. With respect to many aspects of the profile bottom plate 27, it is referred to the above descriptions. In this case, the profile bottom plate 27 at its bottom side being illustrated in FIG. 10 includes a first channel 41, a second channel 42 and a third channel 43. The channels 41, 42 and 43 substantially have an arcuate shape as it generally corresponds to the shape of the bottom plate 27, the correction impression tray 18 and also the jaw of a patient. All channels 41, 42, 43 are connected to the outer rim of the bottom plate 27. The channels 41, 42 are connected to the outer rim to allow for impression material to be introduced into the channels 41, 42 and to exit the channels 41, 42.

Figure 13:
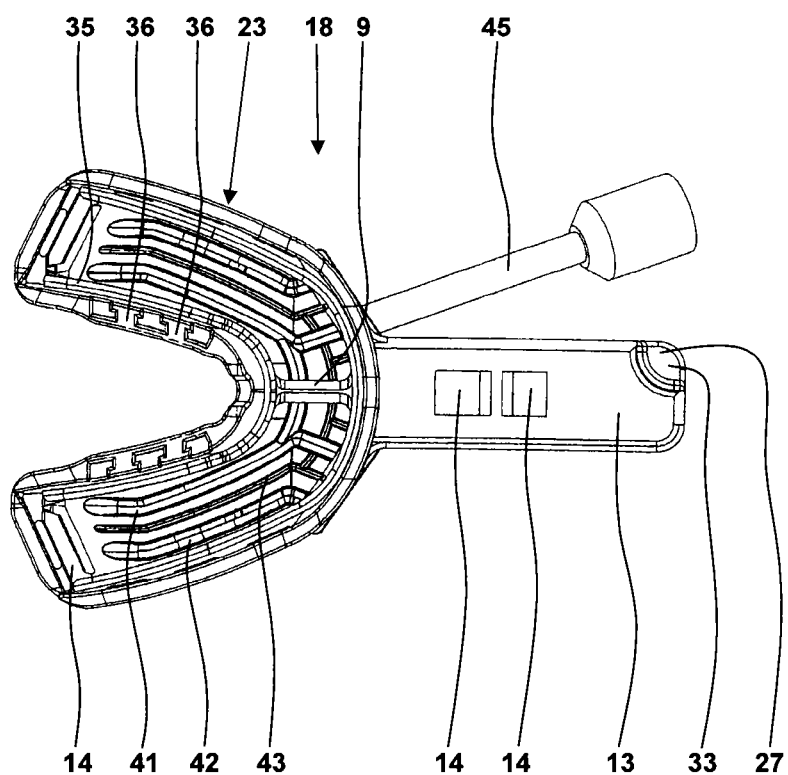
FIG. 13 is a perspective view of the novel injection correction impression tray including a base body being connected to a bottom plate.

In the mounted position of the tray 18 illustrated in FIG. 13, the channels 41, 42 and 43 serve to supply room to be filled with first impression material. The first impression material is supplied from the other side of the tray 18, and it completely fills the tray 18 such that it also enters the channels 41, 42, 43 of the bottom plate 27. In other words, the channels 41, 42, 43 serve to produce protrusions or ribs being made of first impression material. In a following step, the bottom plate 27 can be removed from the base body 23 such that the ribs become accessible. Now, the ribs can be partly removed by the dentist with a knife and the like such that one attains channels. In the next step, the profile bottom plate 27 is once again connected to the base body 23. The channels 41, 42, 43 in the profile bottom plate 27 now together with the channels in the first impression material that have been produced form channels which can be used for introducing the correction impression material and for deaerating purposes (channel 43), respectively. The channels corresponding to the removed ribs being produced by the channels 41, 42 provide the flow path for the correction impression material. The channel resulting from the removed rib being produced by the deaerating channel 43 serves for deaerating purposes such that the preparation chambers 29 can be fully filled with correction impression material and the air previously contained therein can exit the tray 18.

As it is to be seen in FIGS. 10 and 13, the channels 41, 42 have a diameter which is greater than the diameter of the third channel 43. The third channel 43 is connected to the channel 41 which extends almost over the entire length of both legs 32 of the tray 18.

Figure 11:
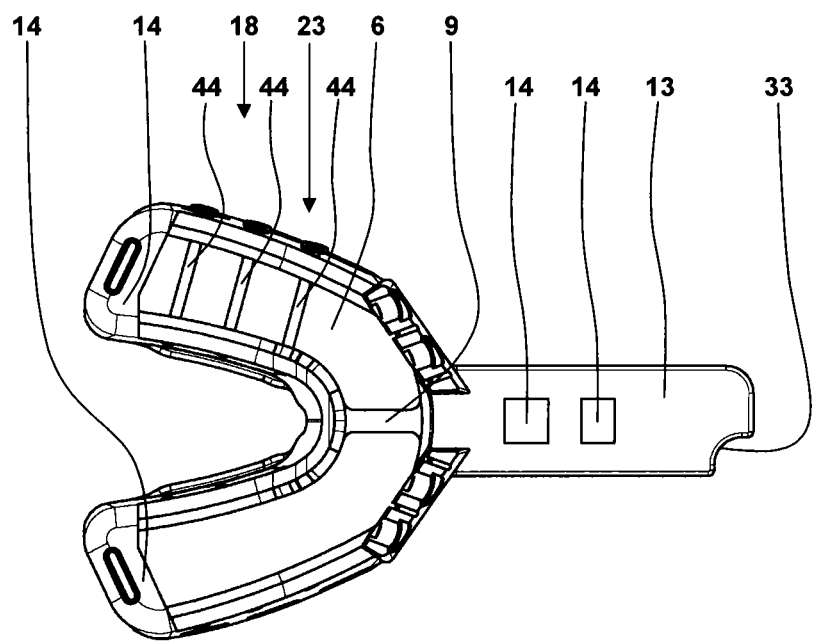
FIG. 11 is a perspective top view of another exemplary embodiment of the base body of the novel injection correction impression tray.
Figure 12:
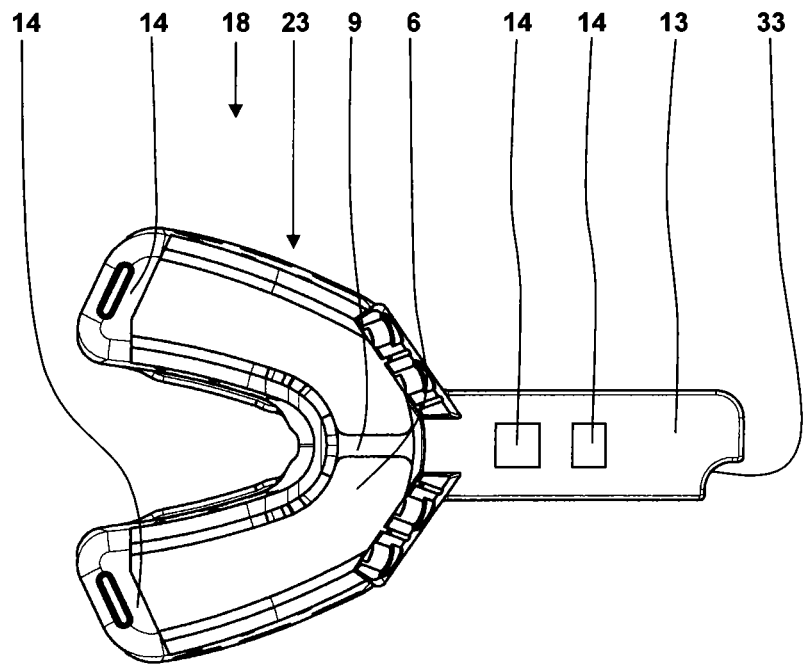
FIG. 12 is a perspective top view of another exemplary embodiment of the base body of the novel injection correction impression tray.

FIG. 11 illustrates the base body 23 including a stationary sinking limiting device 9 and three movable sinking limiting devices 44. The movable sinking limiting devices 44 are designed as pins which can be introduced into the interior of the base body 23 through respective openings in the sidewall of the base body 23. The sinking limiting devices 44 and the sinking limiting device 9 serve to ensure that the teeth of the patient can only be introduced into first impression material contained in the tray 18 until they are stopped by the sinking limiting devices 9, 44. In this way, the teeth are prevented from exiting the base body 23 through the bottom opening 6 and from entering the region of the profile bottom plate 27 and the channels 41, 42, 43.

Furthermore, FIG. 13 illustrates an injection nozzle 45 being connected to the tray 18. The injection nozzle 45 serves to introduce the impression material into the tray 18.

Many variations and modifications may be made to the preferred embodiments of the invention without departing substantially from the spirit and principles of the invention. All such modifications and variations are intended to be included herein within the scope of the present invention, as defined by the following claims.

I claim:

1. An injection correction impression tray for producing dental impressions, comprising:
   a base body, said base body having sidewalls, a bottom opening and an interior, the interior being surrounded by said sidewalls and being designed and arranged to contain impression material; and
   a profile bottom plate,
      said profile bottom plate including two symmetric halves, a first side, and a second side,
      said profile bottom plate including a first channel having a first diameter, at least two second channels having a second diameter and a third channel having a third diameter, said first channel, said second channels and said third channel being arranged in said first side, said first channel substantially having an arcuate shape and extending over a portion of said bottom plate, said first channel being connected to at least one injection channel inlet, each of said second channels extending over a portion of one of said halves, each of said second channels being connected to at least one drainage channel outlet;
      said profile bottom plate being connected to said base body in a way to close said bottom opening and such that said first side and said first channel and said second channels face the interior of said base body;
      said profile bottom plate being designed to be separate from said base body in a way that it can be disconnected from said base body in a non-destructive way;
      said first channel being designed and arranged to form a rib of a first impression material being introduced into the interior of said base body and flowing into said first channel, said first channel being designed and arranged such that a channel for introducing correction impression material is formed by said first channel and a remainder of the first impression material where the rib of the first impression material has been partly removed,
      said second channels each being designed and arranged to form a rib of a first impression material being introduced into the interior of said base body and flowing into said second channels, said second channels being designed and arranged such that a drainage channel is formed by each of said second channels and a remainder of the first impression material where the rib of the first impression material has been partly removed,
      said third channel being designed as a deaerating channel the third diameter of which is smaller than the first and second diameters of said first and second channels.

2. The tray of claim 1, wherein said first diameter of said first channel is greater than said second diameter of said second channels.

3. The tray of claim 1, further comprising at least one sinking limiting device, said sinking limiting device being designed and arranged to limit movement of teeth into first impression material contained in said tray to guarantee sufficient thickness of the first impression material located between the teeth and said profile bottom plate.

4. The tray of claim 2, further comprising at least one sinking limiting device, said sinking limiting device being designed and arranged to limit movement of teeth into first impression material contained in said tray to guarantee sufficient thickness of the first impression material located between the teeth and said profile bottom plate.

5. The tray of claim 3, wherein at least one sinking limiting device is designed as a removable pin, said removable pin being supported in an opening being located in said sidewalls of said base body.

6. The tray of claim 4, wherein at least one sinking limiting device is designed as a removable pin, said removable pin being supported in an opening being located in said sidewalls of said base body.

* * * * *